United States Patent [19]

Buzas et al.

[11] Patent Number: 4,908,365
[45] Date of Patent: Mar. 13, 1990

[54] BENZHYDRYLOXYETHYLPIPERAZINE DERIVATIVES, PROCESSES FOR THEIR PREPARATION AND PHARMACEUTICAL COMPOSITIONS IN WHICH THEY ARE PRESENT

[76] Inventors: André Buzas, 25 Route de Versailles, 91570 Bievres; Jean-Yves Merour, 216 Allée des Pervenches; Roland Ollivier, 94, rue des Fauvettes, both of 45160 Olivet, all of France

[21] Appl. No.: 71,483

[22] Filed: Jul. 7, 1987

[30] Foreign Application Priority Data

Jul. 10, 1986 [FR] France .................. 86 10114

[51] Int. Cl.$^4$ .................. A61K 31/495; C07D 403/06
[52] U.S. Cl. .................. 514/252; 514/253; 514/255; 544/272; 544/285; 544/287; 544/361; 544/370; 544/372; 544/373; 544/397
[58] Field of Search ............. 544/397, 370, 372, 373, 544/361, 285, 287, 272; 514/252, 253, 255

[56] References Cited

U.S. PATENT DOCUMENTS

| | | | |
|---|---|---|---|
| 3,652,568 | 3/1972 | Winter et al. | 544/397 |
| 4,202,896 | 5/1980 | Gootjes | 544/397 |
| 4,377,578 | 5/1983 | Vandenberk et al. | 544/370 |
| 4,675,319 | 6/1987 | Nardi et al. | 544/372 |
| 4,748,247 | 5/1988 | Abou-Gharbia | 544/361 |
| 4,797,488 | 1/1989 | Stack et al. | 544/361 |

FOREIGN PATENT DOCUMENTS

| | | | |
|---|---|---|---|
| 0243903 | 11/1987 | European Pat. Off. | 544/397 |
| 0243905 | 11/1987 | European Pat. Off. | 544/397 |
| 0254627 | 1/1988 | European Pat. Off. | 544/397 |
| 0113226 | 12/1988 | European Pat. Off. | |
| 2235691 | 6/1974 | France. | |
| 2276824 | 7/1974 | France. | |
| 2374318 | 12/1977 | France. | |

Primary Examiner—Glennon H. Hollrah
Assistant Examiner—James H. Turnipseed

[57] ABSTRACT

The present invention relates to benzhydryloxyethylpiperazine derivatives of the formula:

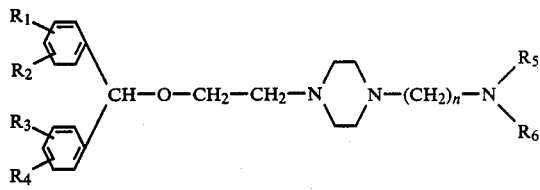

It also relates to processes for the preparation of the said derivatives and pharmaceutical compositions in which they are present. The said derivatives have an antihistaminic activity without a sedative component.

16 Claims, No Drawings

BENZHYDRYLOXYETHYLPIPERAZINE DERIVATIVES, PROCESSES FOR THEIR PREPARATION AND PHARMACEUTICAL COMPOSITIONS IN WHICH THEY ARE PRESENT

The present invention relates to novel benzhydryloxyethylpiperazine derivatives. It also relates to the acid addition salts of these derivatives. It further relates to the processes for the preparation of these derivatives and pharmaceutical compositions in which they are present.

Numerous benzhydrol derivatives having a variety of therapeutic activities are already known. However, these derivatives of the general formula I:

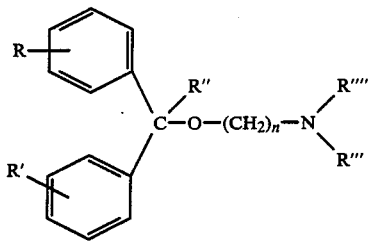

in which R and R' independently of one another represent a hydrogen, an alkyl, an alkoxy or a halogen, R" is either a hydrogen or an alkyl and the unit NR'''R''' represents a substituted dialkylamino, alkylamino, pyrrolidino, piperidino, morpholino or piperazino group, act on the central nervous system and have in particular a sedative component. Reference may be made to the following documents on this subject:

BURGER'S MEDICINAL CHEMISTRY, 4th edition, volume III, Manfred Wolff, p. 559–564, published by WILEY N.Y.

J. M. MELON and A. BUZAS, French Pat. Nos. 74.23.262 and 76.13.592

J. GOOTJES et al., European Pat. No. 0.099.148.

A novel family of compounds has now been found which has an antihistaminic activity identical or even superior to that of the above-mentioned derivatives, but without a sedative component.

The compounds according to the invention are benzhydryloxyethylpiperazine derivatives which correspond to the following general formula:

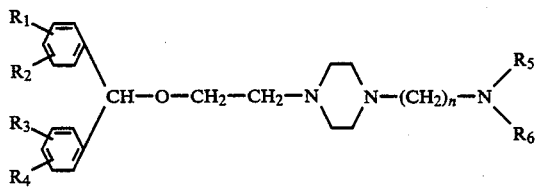

in which
$R_1$, $R_2$, $R_3$ and $R_4$ independently of one another represent a hydrogen atom, a halogen atom, a lower alkyl group, a lower alkoxy group or the trifluoromethyl group;

n is an integer between 1 and 6 inclusive; and $R_5$ and $R_6$ represent in one case a hydrogen atom and in the other a substituted or unsubstituted benzoyl group, or $R_5$ and $R_6$ form, with the nitrogen atom to which they are bonded, a substituted or unsubstituted 5-membered or 6-membered heterocyclic group selected from the following groups: succinimidyl, 4-phenylsuccinimidyl, phthalimidyl, naphthalimidyl, phthalimidinyl, 3-hydroxyphthalimidinyl, 2-oxobenzimidazolinyl, 3-benzyl-2-oxobenzimidazolinyl, 1,2,3,4-tetrahydro-2,4-dioxoquinazolinyl, 3,4-dihydro-4-oxoquinazolinyl, 3,4-dihydro-4-oxo-2-methylquinazolinyl, 3,7-dihydro-1,3-dimethyl-2,6-dioxo-1H-purinyl and 3,7-dihydro-3,7-dimethyl-2,6-dioxo-1H-purinyl.

In the present description, "lower alkyl" denotes saturated or unsaturated aliphatic hydrocarbon radicals containing 1 to 6 carbon atoms; the preferred alkyl group for the purposes of the invention is the methyl group; "lower alkoxy" denotes a hydroxyl group substituted by a lower alkyl as defined above.

For the purposes of the invention, the benzoyl group can be substituted by a hydroxyl, carboxyl or nitro group, preferably in the 2-position.

The compounds of the invention can be obtained by reacting a derivative of the formula III:

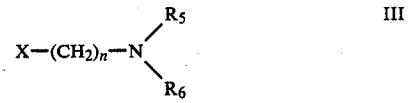

in which n, $R_5$ and $R_6$ are as defined above and X is a halogeno or tosyl group, with an excess of a benzhydryloxyethylpiperazine of the formula IV:

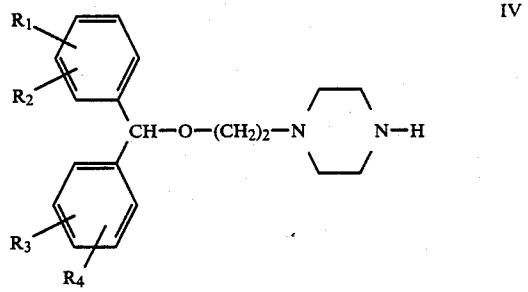

in which $R_1$, $R_2$, $R_3$ and $R_4$ are as defined above, if appropriate in the presence of potassium or sodium iodide.

This reaction is performed by heating under reflux in an appropriate solvent, for example toluene, xylene or methyl ethyl ketone.

This process makes it possible to obtain compounds of the formula II in which $NR_5R_6$ represents one of the following groups in particular: succinimidyl, 4-phenylsuccinimidyl, phthalimidyl, naphthalimidyl, 2-oxobenzimidazolinyl, 3-benzyl-2-oxobenzimidazolinyl, 3,4-dihydro-4oxoquinazolinyl, 3,4-dihydro-2-methyl-4-oxoquinazolinyl, 3,7-dihydro-1,3-dimethyl-2,6-dioxo-1H-purinyl and 3,7-dihydro-3,7-dimethyl-2,6-dioxo-1H-purinyl, 1,2,3,4-tetrahydro-2,4-dioxoquinazolinyl.

The compounds of the formula II in which $-NR_5R_6$ represents the phthalimidinyl group can be obtained by reducing the compound of the formula V below:

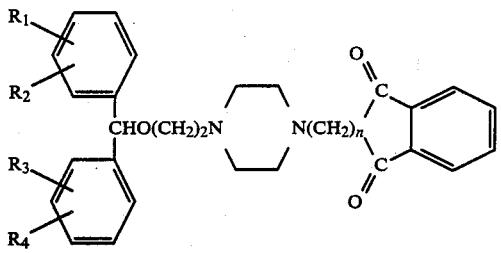

obtained by the above process, this being a compound of the formula II in which $NR_5R_6$ is the phthalimidyl group. The reduction is advantageously carried out in acetic acid at the reflux temperature, in the presence of zinc.

The compounds of the formula II in which $NR_5R_6$ is the 3-hydroxyphthalimidinyl group can advantageously be obtained by reacting a compound of the formula V above with sodium borohydride in appropriate solvents, for example methanol, ethanol or isopropanol.

The compounds of the formula II in which $R_5$ is a hydrogen atom and $R_6$ is a 3-carboxybenzoyl group can be prepared from the compounds of the formula V above, dissolved in a solvent such as tetrahydrofuran (THF), by treatment with an aqueous solution of sodium sulfide at a temperature below 5° C.

Finally, the compounds of the formula II in which $R_4$ represents a hydrogen atom and $R_5$ is a benzoyl group optionally substituted by a hydroxyl group or a nitro group can be obtained by reacting an acid chloride of the formula VI:

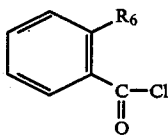

in which $R_6$ is as defined above, with an amine of the formula VII:

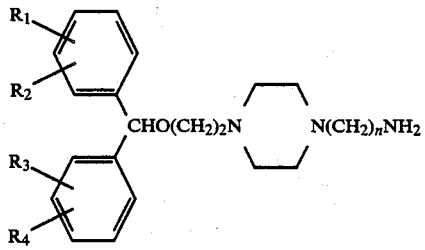

in which $R_1$, $R_2$, $R_3$ and $R_4$ are as defined above, in the presence of pyridine, in an inert solvent such as an aromatic hydrocarbon, for example benzene or toluene, or such as a chlorinated solvent, for example chloroform or methylene chloride.

Acid addition salts of the derivatives according to the invention can be obtained by conventional processes with acids commonly used to obtain pharmaceutically acceptable salts, for example acetic acid, hydrochloric acid, trifluoroacetic acid and methanesulfonic acid.

The compounds according to the invention have valuable pharmacological properties, especially antihistaminic and antispasmodic properties, and are particularly suitable for the treatment of spasmodic states and allergies.

The invention therefore also relates to pharmaceutical compositions in which a derivative according to the invention is present as the active principle, in combination with a pharmaceutically acceptable vehicle. The compositions according to the invention can be administered orally or by injection. They can be in the form of solutions, tablets, pills, gelatin capsules or injectable compositions.

The invention will now be described in greater detail by the illustrative examples below.

The derivatives prepared were identified and characterized by studying their NMR and infrared spectra and also by their elemental analysis.

EXAMPLE 1

1-[2-(Benzhydryloxy)ethyl]-4-[(phthalimido)methyl]-piperazine dimethanesulfonate (1)

7.35 g of phthalimide, 14.8 g of benzhydryloxyethylpiperazine and 70 ml of absolute ethanol were placed in a reactor. 5 ml of a 35% solution of formaldehyde were added dropwise at 0° C. The reaction mixture was stirred for 10 minutes at this temperature. The precipitate was filtered off and recrystallized from 50 ml of ethanol (m.p.=124° C.).

3.7 g of methanesulfonic acid were added to the 9 g of product obtained, dissolved in 50 ml of acetone. The solid was filtered off to give 12.2 g of the dimethanesulfonate (m.p.=116° C.) of the empirical formula: $C_{28}H_{29}N_3O_3.2(CH_4O_3S)$.

Elemental analysis:

% calculated: C=55.64; H=5.72; N=6.49; S=9.89;
% found: C=55.56; H=5.48; N=6.48; S=9.82.

NMR spectrum (base, $CDCl_3$, internal reference TMS):

7.5 ppm (m), 4H, (phthalimido); 7.0 ppm (s), 10H, ($\phi_2C$);

5.1 ppm (s), 1H, (CH—O); 4.4 ppm (s), 2H, (N—CH$_2$—N);

3.4 ppm (t), 2H, ($CH_2$—O); 2.5 ppm (m), 10H, ($CH_2$—N).

IR spectrum (1% in KBr):

1780 cm$^{-1}$ (C=O asym.), 1710 cm$^{-1}$ (C=O sym.), 1190 cm$^{-1}$ ($SO_2$), 1050 cm$^{-1}$ ($SO_2$).

EXAMPLE 2

1-[2-(Benzhydryloxy)ethyl]-4-[2-(phthalimido)-ethyl]-piperazine dimethanesulfonate (2)

15.3 g of bromoethylphthalimide, 36 g of benzhydryloxyethylpiperazine, 500 mg of potassium iodide and 250 ml of anhydrous toluene were placed in a reactor. The reaction mixture was heated for 6 hours at 120° C. The residue was taken up with 100 ml of water. A further extraction was carried out with 100 ml of toluene. The extract was dried and the solvents were evaporated off to give 27 g of an oil which crystallized from ethanol. The solid was filtered off and 25.5 g of crystals (m.p.=101° C.) were collected.

10.5 g of methanesulfonic acid were added to these 25.5 g of solid, dissolved in 100 ml of acetone. The product was filtered off to give 34 g of the dimethanesulfonate (m.p.=124° C.) of the empirical formula: $C_{29}H_{31}N_3O_3.2(CH_4O_3S)$.

Elemental analysis:

% calculated: C=59.26; H=5.94; N=6.35; S=9.69;

% found: C=59.24; H=5.99; N=6.36; S=9.79.

NMR spectrum (base in solution in CDCl$_3$, reference TMS):

7.6 ppm (m), 4H, (phthalimido); 7.1 ppm (m), 10H, ($\phi_2$C);

5.3 ppm (s), 1H, (CH—O); 3.8 ppm (t), 2H, (CH$_2$—N—C=O);

3.5 ppm (t), 2H, (CH$_2$—O); 2.5 ppm (m), 12H, (CH$_2$—N).

IR spectrum (1% in KBr):

1780 cm$^{-1}$ (C=O asym.), 1710 cm$^{-1}$ (C=O sym.), 1200 cm$^{-1}$ (SO$_2$), 1070 cm$^{-1}$ (SO$_2$).

EXAMPLE 3

1-[2-(Benzhydryloxy)ethyl]-4-[2-(phthalimidino)ethyl]piperazine dimethanesulfonate (22)

12 g of 1-[2-(benzhydryloxy)ethyl]-4-[2-(phthalimido)ethyl]piperazine, 8.4 g of zinc and 45 ml of glacial acetic acid were placed in a reactor. The mixture was heated under reflux for 5 hours. It was taken up with 100 ml of 2 N hydrochloric acid and 100 ml of benzene. After decantation, the aqueous phase was rendered alkaline with NaHCO$_3$ in the presence of 100 ml of methylene chloride. After drying, the solvents were evaporated off to give 7.4 g of a solid which recrystallized from ethanol (m.p.=107° C.).

The dimethanesulfonate was prepared in acetone by reacting the solid with 3.2 g of methanesulfonic acid. This gave 10.3 g of the dimethanesulfonate (m.p.=135° C.) of the empirical formula: C$_{29}$H$_{33}$N$_3$O$_2$.2(CH$_4$O$_3$S).

Elemental analysis:

% calculated: C=57.50; H=6.34; N=6.41; S=9.89;

% found: C=57.61; H=6.48; N=5.53; S=9.95.

NMR spectrum (base in solution in CDCl$_3$, reference TMS):

7.5 ppm (m), 1H, (phthalimido); 7.1 ppm (s), 10H, ($\phi_2$C);

6.2 to 7.4 ppm (m), 3H, (phthalimido); 5.2 ppm (s), 1H, (CHO); 4.3 ppm (s), 2H, (N—CH$_2$-$\phi$); 3.6 ppm (t), 2H, (CH$_2$N—C=O); 3.4 ppm (t), 2H, (CH$_2$—O); 2.6 ppm (m), 12H, (CH$_2$—N).

IR spectrum (1% in KBr):

1665 cm$^{-1}$ (C=O), 1230 cm$^{-1}$ (SO$_2$), 1070 cm$^{-1}$ (SO$_2$).

EXAMPLE 4

1-[2-(Benzhydryloxy)ethyl]-4-[(3-hydroxyphthalimidino)ethyl]piperazine dimethanesulfonate (23)

15 g of 1-[2-(benzhydryloxy)ethyl]-4-[2-(phthalimido)ethyl]piperazine and 100 ml of methanol at 90° C. were placed in a reactor. A solution of 4.8 g of sodium borohydride in 100 ml of methanol was added dropwise at 30° C. over a period of 30 minutes. The mixture was stirred for 7 hours at 30° C. and then for 10 hours at room temperature. The solution was filtered and the solvents were evaporated off. The oil was taken up with 100 ml of benzene. 50 ml of 1 N hydrochloric acid were added and the precipitate formed was filtered off. The aqueous phase was rendered alkaline with NaHCO$_3$ in the presence of methylene chloride (100 ml). After drying, the solvents were evaporated off. 6.4 g of a colorless oil were collected.

The dimethanesulfonate was prepared by reacting the product obtained, dissolved in ether, with methanesulfonic acid. This gave a solid (m.p.=98° C.) of the empirical formula: C$_{29}$H$_{33}$N$_3$O$_3$.2(CH$_4$O$_3$S).

Elemental analysis:

% calculated: C=56.10; H=6.18; N=6.33; S=9.65;

% found: C=56.09; H=6.15; N=6.28; S=9.52.

NMR spectrum (base in solution in CDCl$_3$, reference TMS):

6.9 to 7.6 ppm (m), 14H, (aromatic protons); 5.4 ppm (s), 1H, (CHOH); 5.1 ppm (s), 1H, (CH—O); 4.5 ppm (s), 1H, (OH); 3.8 ppm (t), 2H, (CH$_2$—N—CO); 3.3 ppm (t), 2H, (CH$_2$O); 2.5 ppm (m), 12H, (CH$_2$N).

IR spectrum (1% in KBr):

3240 cm$^{-1}$ (OH), 1680 cm$^{-1}$ (C=O), 1200 cm$^{-1}$ (SO$_2$), 1060 cm$^{-1}$ (SO$_2$).

EXAMPLE 5

1-[2-(Benzhydryloxy)ethyl]-4-[(2-carboxybenzamido)ethyl]piperazine (36)

20 g of 1-[2-(benzhydryloxy)ethyl]-4-[2-(phthalimido)ethyl]piperazine and 200 ml of tetrahydrofuran were placed in a reactor. A solution of 20.4 g of Na$_2$S.9H$_2$O in 80 ml of water was added dropwise at 0° C. After decantation, the solvents were evaporated off. The solid was taken up in 50 ml of water and 100 ml of methylene chloride. After the solution had cooled, the pH was adjusted to 3.7 and extraction was carried out with 2 times 50 ml of methylene chloride. After drying, the solvents were evaporated off to give 17 g of a solid (m.p.=45° C.) of the empirical formula: C$_{29}$H$_{33}$N$_3$O$_4$.

Elemental analysis:

% calculated: C=71.46; H=6.78; N=8.62;

% found: C=71.42; H=6.74; N=8.70.

NMR spectrum (solvent CDCl$_3$, internal reference TMS):

10 ppm (s), 1H, (COOH); 7.8 ppm (s), 1H, (NH); 6.7 to 7.3 ppm (m), 14H, ($\phi$); 5.0 ppm (s), 1H, (CH—O); 2.2 to 3.7 ppm (m), 16H, (CH$_2$—N).

IR spectrum (1% in KBr):

3200 cm$^{-1}$ (OH), 1650 cm$^{-1}$ (C=O).

EXAMPLES 6 to 38

The compounds shown in the table below were obtained by repeating one of the procedures of Examples 1 to 5; the table also shows the compounds of Examples 1 to 5 above.

TABLE I (General structure: two phenyl rings with substituents $R_1, R_2, R_3, R_4$ connected via CH—O—CH$_2$—CH$_2$—N (piperazine) N—(CH$_2$)$_n$—CR$_5$R$_6$)

| No. | $R_1$ | $R_2$ | $R_3$ | $R_4$ | N | NR$_5$R$_6$ | Empirical formula | Salt | Melting point °C. | Prepared according to example no. |
|---|---|---|---|---|---|---|---|---|---|---|
| 1 | H | H | H | H | 1 | phthalimido | $C_{28}H_{29}N_3O_3$ | 2CH$_3$SO$_3$H | 116 | 1 |
| 2 | H | H | H | H | 2 | phthalimido | $C_{29}H_{31}N_3O_3$ | 2CH$_3$SO$_3$H | 124 | 2 |
| 3 | H | H | H | H | 2 | isoindolinon-yl | $C_{29}H_{33}N_3O_2$ | 2CH$_3$SO$_3$H | 135 | 3 |
| 4 | H | H | H | H | 2 | 3-hydroxy-isoindolinon-yl | $C_{29}H_{33}N_3O_3$ | 2CH$_3$SO$_3$H | 98 | 4 |
| 5 | H | H | H | H | 2 | —NH—CO—(2-hydroxyphenyl) | $C_{28}H_{33}N_3O_3$ | 2CH$_3$SO$_3$H |  | 5 |
| 6 | 4-F | H | H | H | 2 | phthalimido | $C_{29}H_{30}FN_3O_3$ | 2CH$_3$SO$_3$H | 133 | 2 |
| 7 | 4-Cl | H | H | H | 2 | phthalimido | $C_{29}H_{30}ClN_3O_3$ | 2CH$_3$SO$_3$H | 141 | 2 |
| 8 | 4-CH$_3$O | H | H | H | 2 | phthalimido | $C_{30}H_{33}N_3O_4$ | 2CH$_3$SO$_3$H |  | 2 |
| 9 | 4-CH$_3$O | H | H | H | 2 | phthalimido | $C_{30}H_{33}N_3O_4$ | 2C$_4$H$_4$O$_4$ | 179 | 2 |
| 10 | 2-Cl | H | H | H | 2 | phthalimido | $C_{29}H_{29}ClN_3O_3$ | 2CH$_3$SO$_3$H | 94 | 2 |
| 11 | 3-CF$_3$ | H | H | H | 2 | phthalimido | $C_{30}H_{30}F_3N_3O_3$ | 2CH$_3$SO$_3$H |  | 2 |
| 12 | 4-CH$_3$ | H | H | H | 2 | phthalimido | $C_{30}H_{33}N_3O_3$ | 2CH$_3$SO$_3$H | 143 | 2 |
| 13 | 3-CH$_3$O | H | H | H | 2 | phthalimido | $C_{30}H_{33}N_3O_4$ | 2CH$_3$SO$_3$H | 150 | 2 |
| 14 | 3-Cl | H | H | H | 2 | phthalimido | $C_{29}H_{30}ClN_3O_3$ | 2CH$_3$SO$_3$H | 156 | 2 |
| 15 | 4-Cl | H | 4-Cl | H | 2 | phthalimido | $C_{29}H_{29}Cl_2N_3O_3$ | 2CH$_3$SO$_3$H | 190 | 2 |
| 16 | 2-Cl | 6-Cl | H | H | 2 | phthalimido | $C_{29}H_{29}Cl_2N_3O_3$ | 2CH$_3$SO$_3$H | 175 | 2 |
| 17 | 2-CF$_3$ | H | 2-CF$_3$ | H | 2 | phthalimido | $C_{31}H_{29}F_6N_3O_3$ | 2CH$_3$SO$_3$H |  | 2 |
| 18 | H | H | H | H | 3 | phthalimido | $C_{30}H_{33}N_3O_3$ | 2CH$_3$SO$_3$H | 144 | 2 |
| 19 | H | H | H | H | 4 | phthalimido | $C_{31}H_{35}N_3O_3$ | 2CH$_3$SO$_3$H |  | 2 |
| 20 | H | H | H | H | 5 | phthalimido | $C_{32}H_{37}N_3O_3$ | 2CH$_3$SO$_3$H |  | 2 |
| 21 | H | H | H | H | 6 | phthalimido | $C_{33}H_{39}N_3O_3$ | 2CH$_3$SO$_3$H |  | 2 |
| 22 | H | H | H | H | 2 | succinimido | $C_{25}H_{31}N_3O_3$ | 2CH$_3$SO$_3$H | 105 | 2 |
| 23 | H | H | H | H | 2 | phenyl-succinimido | $C_{31}H_{35}N_3O_3$ | 2CH$_3$SO$_3$H | 110 | 2 |

TABLE I-continued
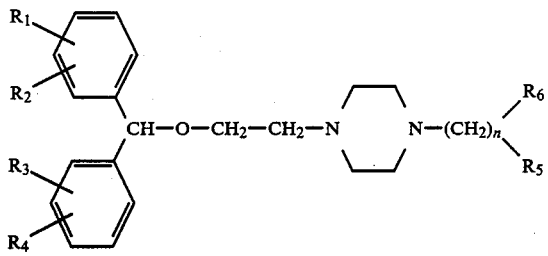
| No. | R₁ | R₂ | R₃ | R₄ | N | NR₅R₆ | Empirical formula | Salt | Melting point °C. | Prepared according to example no. |
|---|---|---|---|---|---|---|---|---|---|---|
| 24 | H | H | H | H | 2 | 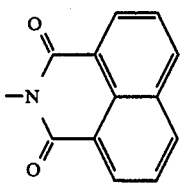 | $C_{33}H_{33}N_3O_3$ | $2CH_3SO_3H$ | >200 | 2 |
| 25 | H | H | H | H | 2 | 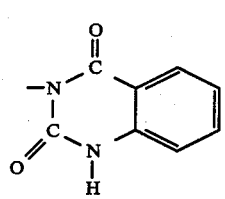 | $C_{29}H_{32}N_4O_3$ | $2CH_3SO_3H$ | 194 | 2 |
| 26 | H | H | H | H | 2 | 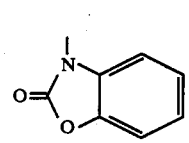 | $C_{29}H_{33}N_3O_3$ | $2CH_3SO_3H$ | 172 | 2 |
| 27 | H | H | H | H | 2 | 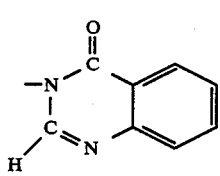 | $C_{29}H_{32}N_4O_2$ | $2CH_3SO_3H$ | | 2 |
| 28 | H | H | H | H | 2 | 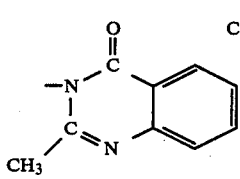 | $C_{30}H_{34}N_4O_2$ | $2CH_3SO_3H$ | | 2 |
| 29 | H | H | H | H | 2 | 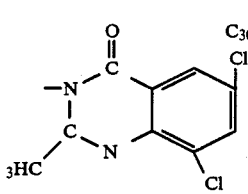 | $C_{30}H_{32}Cl_2N_4O_2$ | $2CH_3SO_3H$ | 148 | 2 |
| 30 | H | H | H | H | 2 | 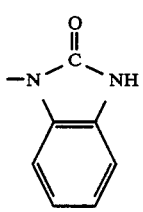 | $C_{28}H_{32}N_4O_2$ | $2CH_3SO_3H$ | | 2 |
| 31 | H | H | H | H | 3 | | $C_{29}H_{34}N_4O_2$ | $2CH_3SO_3H$ | | 2 |

TABLE I-continued $$\text{Structure: } (R_1,R_2)\text{-C}_6H_3\text{-CH(O-CH}_2\text{-CH}_2\text{-N(piperazine)N-(CH}_2)_n\text{-R}_5,R_6)\text{-C}_6H_3\text{-}(R_3,R_4)$$

| No. | R₁ | R₂ | R₃ | R₄ | N | NR₅R₆ | Empirical formula | Salt | Melting point °C. | Prepared according to example no. |
|---|---|---|---|---|---|---|---|---|---|---|
| 32 | H | H | H | H | 2 | −N−C(=O)−N(CH₂φ) (benzimidazolone) | $C_{35}H_{38}N_4O_2$ | 2CH₃SO₃H | 173 | 2 |
| 33 | H | H | H | H | 2 | theophylline | $C_{28}H_{34}N_6O_3$ | 2CH₃SO₃H | | 2 |
| 34 | H | H | H | H | 4 | | $C_{30}H_{38}N_6O_3$ | 2CH₃SO₃H | | 2 |
| 35 | 4-F | H | H | H | 2 | theophylline | $C_{28}H_{33}FN_6O_3$ | 2CH₃SO₃H | 156 | 2 |
| 36 | 4-CH₃ | H | H | H | 2 | | $C_{29}H_{36}N_6O_3$ | 2CH₃SO₃H | 160 | 2 |
| 37 | 4-Cl | H | H | H | 2 | | $C_{28}H_{33}N_6ClO_3$ | 2CH₃SO₃H | 159 | 2 |
| 38 | 4-Cl | H | 4-Cl | H | 2 | | $C_{28}H_{32}Cl_2N_6O_3$ | 2CH₃SO₃H | 175 | 2 |
| 39 | 4-CH₃O | H | H | H | 2 | | $C_{29}H_{36}N_6O_4$ | 2CH₃SO₃H | 154 | 2 |
| 40 | 2-Cl | H | H | H | 2 | | $C_{28}H_{33}ClN_6O_3$ | 2CH₃SO₃H | 154 | 2 |
| 41 | 4-CH₃ | H | H | H | 4 | | $C_{31}H_{40}N_6O_3$ | 2CH₃SO₃H | | 2 |
| 42 | 4-F | H | H | H | 4 | | $C_{30}H_{37}FN_6O_3$ | 2CH₃SO₃H | | 2 |
| 43 | 4-Cl | H | H | H | 4 | | $C_{30}H_{37}ClN_6O_3$ | 2CH₃SO₃H | 172 | 2 |
| 44 | 4-F | H | 4-F | H | 2 | | $C_{28}H_{32}F_2N_6O_3$ | 2CH₃SO₃H | 164 | 2 |
| 45 | 4-Cl | H | 4-Cl | H | 4 | | $C_{30}H_{36}Cl_2N_6O_3$ | 2CH₃SO₃H | | 2 |
| 46 | 4-CH₃O | H | H | H | 4 | | $C_{31}H_{40}N_6O_4$ | 2CH₃SO₃H | | 2 |
| 47* | H | H | H | H | 2 | threobromine | $C_{28}H_{34}N_6O_3$ | 2CH₃SO₃H | | 2 |
| 48 | H | H | H | H | 2 | −NH−C(=O)−C₆H₄(HOOC-) | $C_{29}H_{33}N_3O_4$ | base | 45 | 2 |
| 49 | H | H | H | H | 2 | −NH−C(=O)−C₆H₄(NO₂-) | $C_{28}H_{32}N_4O_4$ | 2CH₃SO₃H | 170 | 2 |
| 50 | H | H | H | H | 3 | −NH−C₆H₄(NO₂-) | $C_{29}H_{34}N_4O_3$ | 2C₄H₄O₄ | 180 | 2 |

The toxicity of the compounds of the invention was determined by the following procedure:

I-TOXICITY TEST

Determination of the 50% lethal dose ($LD_{50}$) in mice.

The derivatives studied were administered intraperitoneally to groups made up of five male mice and five female mice, at a rate of 0.1 ml per ten grams of body weight. The 50% lethal dose was evaluated from the mortality observed.

The results obtained are reproduced in Table II below:

TABLE II

| Derivative number | $LD_{50}$ mg.kg⁻¹ i.p. |
|---|---|
| 2 | 211 |
| 19 | 133 |
| 22 | 146 |
| 32 | 400 |
| 33 | 240 |
| 5 | 185 |
| 36 | 178 |
| 49 | 131 |

II-PHARMACOLOGICAL TESTS

The pharmacological properties of the compounds of the invention were determined using the following tests:

Test protocols

A-Study of the spontaneous motility

The motor activity of mice was determined with the aid of a Boissier and Simon photoelectric actimeter.

The mice are placed in groups of five in a box closed with a lid, through which two perpendicular light rays pass; the mice cut off these rays when they move.

These movements are measured by a counter, which is read after thirty minutes and one hour.

B-Exploration behavior

Thirty minutes after the intraperitoneal administration of the derivatives according to the invention, each mouse is placed on an automated hole-board for five minutes and the number of holes explored is noted every minute.

A 50% effective dose can be calculated from the results obtained.

C-Muscle-relaxing action (traction test)

This test assesses the presence or absence of redressments in a mouse brought up to a horizontal wire with its front paws.

The number of mice which are unable to grip the wire with one of their back paws within five seconds are noted.

A 50% effective dose can be calculated from the results obtained.

D-Interaction with pentobarbital

This test tries to measure any increase in the sleep induced by pentobarbital which is caused by administering the test product intraperitoneally five minutes before the intraperitoneal injection of pentobarbital.

A 50% effective dose can be calculated from the results obtained.

E-Peripheral analgesic activity

A peritoneal pain is caused in mice by the intraperitoneal injection of phenylbenzoquinone (PBQ). The test tries to measure the decrease in the pain syndrome, characterized by an abdominal twisting movement, which is caused by injecting the test product thirty minutes before the administration of PBQ.

The 50% effective dose is calculated from the percentage decrease in the pain syndrome relative to the control animals.

F-Bronchospasm by inhalation of a histamine solution

Guinea-pigs are placed in a closed chamber into which histamine is introduced as an aerosol, and only those which show very distinct signs of asphyxia within four minutes are selected.

The substance to be studied is administered to groups of guinea-pigs thirty minutes before a further period in the chamber in order to check the resistance to histamine. A guinea-pig is considered to be protected if it resists the histamine aerosol for ten minutes without showing signs of asphyxia.

A 50% effective dose is calculated from the results obtained.

G-Antihistaminic activity

This test tries to measure the dose which protects fifty percent of the guinea-pigs from a lethal dose of histamine.

The product is administered thirty minutes before the intravenous injection of histamine hydrochloride.

The 50% effective dose is calculated from the results obtained.

Results

The results obtained are collated in Table III below.

Comparative tests

By way of comparison, the above tests were carried out with Terfenadine as a compound of the prior art; this compound gave the following results in the various tests defined above;

| MICE | |
|---|---|
| Toxicity by intraperitoneal administration | $LD_{50} = 100$ mg.kg$^{-1}$ i.p. |
| Motor activity | Significant decrease at 25 mg.kg$^{-1}$ i.p. |
| Exploration behavior | $ED_{50} = 37$ mg.kg$^{-1}$ i.p. |
| Muscle-relaxing action - Traction test | $ED_{50} = 31$ mg.kg$^{-1}$ i.p. |
| Interaction with pentobarbital | $ED_{50} + 25$ mg.kg$^{-1}$ i.p. |
| Peripheral analgesic activity | $ED_{50} = 3.1$ mg.kg$^{-1}$ i.p. |
| GUINEA-PIGS | |
| Bronchospasm by oral administration | $ED_{50} = 1.60$ mg.kg$^{-1}$ p.o. |
| Histaminic shock by oral administration | $ED_{50} = 2.58$ mg.kg$^{-1}$ p.o. |

The results obtained with the compounds of the invention are shown in Table III.

These results show that the antihistaminic activity of the compounds of the invention is substantially equivalent or superior to that of the prior art compound tested, but the compounds of the invention do not possess a sedative component.

TABLE III

Results of pharmacological tests

| Derivative number | Motor activity (mouse) mg.kg$^{-1}$ i.p. | Exploration behavior (mouse) mg.kg$^{-1}$ i.p. | Muscle-relaxing action Traction test (mouse) mg.kg$^{-1}$ i.p. | Interaction with pentobarbital (mouse) mg.kg$^{-1}$ i.p. | Peripheral analgesic activity (mouse) $ED_{50}$ mg.kg$^{-1}$ | Bronchospasm (guinea-pig) $ED_{50}$ mg.kg$^{-1}$ | Histaminic shock (guinea-pig) $ED_{50}$ mg.kg$^{-1}$ |
|---|---|---|---|---|---|---|---|
| Compounds of the invention | | | | | | | |
| 2 | no modification at 50 | no modification at 50 | no modification at 100 | no interaction at 25 | 3.12 (i.p.) | 3.67 (i.p.) | 2.03 (i.p.) |
| 19 | no | no | no | no | 1.56 (i.p.) | 5.34 (p.o.) | 2.20 (p.o.) |

TABLE III-continued

| | Results of pharmacological tests | | | | | | |
|---|---|---|---|---|---|---|---|
| Derivative number | Motor activity (mouse) mg.kg$^{-1}$ i.p. | Exploration behavior (mouse) mg.kg$^{-1}$ i.p. | Muscle-relaxing action Traction test (mouse) mg.kg$^{-1}$ i.p. | Interaction with pentobarbital (mouse) mg.kg$^{-1}$ i.p. | Peripheral analgesic activity (mouse) ED$_{50}$ mg.kg$^{-1}$ | Bronchospasm (guinea-pig) ED$_{50}$ mg.kg$^{-1}$ | Histaminic shock (guinea-pig) ED$_{50}$ mg.kg$^{-1}$ |
| | modification at 25 | modification at 25 | modification at 25 | interaction at 25 | | | |
| 22 | no modification at 25 | no modification at 12.5 | no modification at 25 | no interaction at 25 | 35 (p.o.) | 3.96 (i.p.) | 3.25 (i.p.) |
| 32 | no modification at 25 | no modification at 25 | no modification at 25 | no interaction at 6.25 | — | 33% at 12.5 (p.o.) | 2.30 (p.o.) |
| 33 | no modification at 12.5 | no modification at 25 | no modification at 25 | no interaction at 12.5 | 0 | 0.59 (p.o.) | 2.57 (p.o.) |
| 5 | increase in activity | no modification at 25 | no modification at 25 | no interaction at at 25 | 6.25 (s.c.) | 2.06 (i.p.) | 5.24 (p.o.) |
| 36 | increase at weak dose - no modification at strong dose | no modification at 25 | no modification at 25 | no modification at 25 | 1.56 (s.c.) | 0.19 (p.o.) | 0.55 (p.o.) |
| 49 | increase in activity | no modification at 25 | | no interaction at 25 | 2.6 (s.c.) | 3.125 (p.o.) | |

What is claimed is:

1. Benzhydryloxyethylpiperazine derivatives corresponding to the formula II:

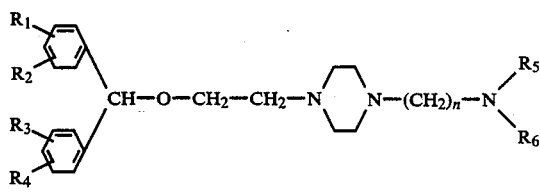

in which:

R$_1$, R$_2$, R$_3$, R$_4$ independently of one another represent a hydrogen atom, a halogen atom, a lower alkyl group, a lower alkoxy group or the trifluoromethyl group;
n is an integer between 1 and 6 inclusive; and
R$_5$ and R$_6$ represent in one case a hydrogen atom and in the other a benzoyl or benzoyl substituted with a member selected from the group consisting of hydroxyl, carboxyl and nitro, or R$_5$ and R$_6$ form, with the nitrogen atom to which they are bonded, a 5-membered or 6-membered heterocyclic group selected from the following groups: succinimidyl, 4-phenylsuccinimidyl, phthalimidyl, napthalimidyl, phthalimidinyl, 3-hydroxyphthalimidinyl, 2-oxobenzimidazolinyl, 3-benzyl-2-oxobenzimidazolinyl, 1,2,3,4-tetrahydro-2,4-dioxoquinazolinyl, 3,4-dihydro-4-oxoquinazolinyl, 3,4-dihydro-4-oxo-2-methylquinazolinyl, 3,7-dihydro-1,3-dimethyl-2,6-dioxo-1H-purinyl and 3,7-dihydro-3,7-dimethyl-2,6-dioxo-1H-purinyl.

2. The benzhydryloxyethylpiperazine derivative of claim 1 wherein:
R$_1$, R$_2$, R$_3$, and R$_4$ are each a hydrogen atom;
n is 2; and
R$_5$ and R$_6$ form, with the nitrogen atom to which they are bonded,

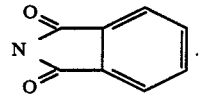

3. The benzhydryloxyethylpiperazine derivative of claim 1 wherein:
R$_1$, R$_2$, R$_3$, and R$_4$ are each a hydrogen atom;
n is 4; and
R$_5$ and R$_6$ form, with the nitrogen atom to which they are bonded, theophylline.

4. The benzhydryloxyethylpiperazine derivative of claim 1 wherein:
R$_1$ is 4—CH$_3$, R$_2$, R$_3$, and R$_4$ are each a hydrogen atom;
n is 2; and
R$_5$ and R$_6$ form, with the nitrogen atom to which they are bonded, theophylline.

5. The benzhydryloxyethylpiperazine derivative of claim 1 wherein:
R$_1$, R$_2$, R$_3$, and R$_4$ are each a hydrogen atom;
n is an integer between 1 and 3, inclusive; and
R$_5$ and R$_6$ form, with the nitrogen atom to which they are bonded, one of the radicals as defined in Table I.

6. The benzhydryloxyethylpiperazine derivative of claim 1 wherein:
R$_1$ is selected from the group consisting of 4—F, 4—Cl, 4—CH$_3$O, 2—Cl, 3—CF$_3$, 4—CH$_3$, 3—CH$_3$O, or 3—Cl;
R$_2$, R$_3$, and R$_4$ are each a hydrogen atom;
n is 2; and
R$_5$ and R$_6$ form, with the nitrogen atom to which they are bonded,

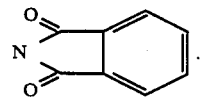

7. The benzhydryloxyethylpiperazine derivative of claim 1 wherein:
$R_1$ and $R_3$ are each 4—Cl;
$R_2$ and $R_4$ are each a hydrogen atom;
n is 2; and
$R_5$ and $R_6$ form, with the nitrogen atom to which they are bonded, a radical selected from the group consisting of theophylline or

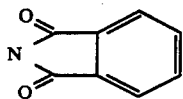

8. The benzhydryloxyethylpiperazine derivative of claim 1 wherein:
$R_1$, $R_2$, $R_3$, and $R_4$ are each a hydrogen atom;
n is an integer between 3 and 6, inclusive; and
$R_5$ and $R_6$ form, with the nitrogen atom to which they are bonded,

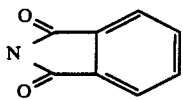

9. The benzhydryloxyethylpiperazine derivative of claim 1 wherein:
$R_1$ is 2—Cl, $R_2$ is 6—Cl, $R_3$ and $R_4$ are each a hydrogen atom;
n is 2; and
$R_5$ and $R_6$ form, with the nitrogen atom to which they are bonded,

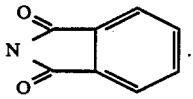

10. The benzhydryloxyethylpiperazine derivative of claim 1 wherein:
$R_1$ and $R_3$ are each 2—CF$_3$;
$R_2$ and $R_4$ are each a hydrogen atom;
n is 2; and
$R_5$ and $R_6$ form, with the nitrogen atom to which they are bonded,

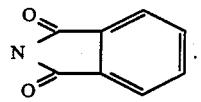

11. The benzhydryloxyethylpiperazine derivative of claim 1 wherein:
$R_1$, $R_2$, $R_3$, and $R_4$ are each a hydrogen atom;
n is 4; and
$R_5$ and $R_6$ form, with the nitrogen atom to which they are bonded, theophylline.

12. The benzhydryloxyethylpiperazine derivative of claim 1 wherein:
$R_1$ is selected from the group consisting of 4—F, 4—CH$_3$, 4—Cl, 4—CH$_3$O, or 2—Cl;
$R_2$, $R_3$, and $R_4$ are each a hydrogen atom;
n is 2; and
$R_5$ and $R_6$ form, with the nitrogen atom to which they are bonded, theophylline.

13. The benzhydryloxyethylpiperazine derivative of claim 1 wherein:
$R_1$ is selected from the group consisting of 4—CH$_3$, 4—Cl, or 4—CH$_3$O;
$R_2$, $R_3$, and $R_4$ are each a hydrogen atom;
n is 4; and
$R_5$ and $R_6$ form, with the nitrogen atom to which they are bonded, theophylline.

14. The benzhydryloxyethylpiperazine derivative of claim 1 wherein:
$R_1$ and $R_3$ are each 4—F;
$R_2$ and $R_4$ are each a hydrogen atom;
n is 2; and
$R_5$ and $R_6$ form, with the nitrogen atom to which they are bonded, theophylline.

15. The benzhydryloxyethylpiperazine derivative of claim 1 wherein:
$R_1$ and $R_3$ are each 4—Cl;
$R_2$ and $R_4$ are each a hydrogen atom;
n is 4; and
$R_5$ and $R_6$ form, with the nitrogen atom to which they are bonded, theophylline.

16. Pharmaceutical compositions which contain a derivative as claimed in claim 1 as the active ingredient, in combination with a pharmaceutically acceptable vehicle.

* * * * *